United States Patent [19]

Boelema et al.

[11] 4,443,561
[45] Apr. 17, 1984

[54] PROCESS FOR THE PREPARATION OF ORGANIC COMPOUNDS

[75] Inventors: Sikko J. A. Boelema, The Hague; Martin F. M. Post; Swan T. Sie, both of Amsterdam, all of Netherlands

[73] Assignee: Shell Oil Company, Houston, Tex.

[21] Appl. No.: 381,619

[22] Filed: May 24, 1982

[30] Foreign Application Priority Data

Jul. 17, 1981 [NL] Netherlands .................. 8103397

[51] Int. Cl.$^3$ .................. C07C 1/04; C07C 27/06
[52] U.S. Cl. .................. 518/704; 518/707; 518/706
[58] Field of Search .................. 518/704, 707, 706

[56] References Cited

U.S. PATENT DOCUMENTS 4,338,089  7/1982  Shaper et al. .................. 518/707

Primary Examiner—Howard T. Mars
Attorney, Agent, or Firm—John M. Duncan

[57] ABSTRACT

In a two-stage process for the conversion of $H_2$-poor syngas into hydrocarbons and oxygenates in which uncoverted syngas from the first stage product is converted in a second stage into paraffins over a Ni, Co or Ru catalyst, the $H_2$/CO molar ratio of the feed for the second stage is adjusted to the required value of 1.75-2.25 by blending this feed with an $H_2$-rich syngas with an $H_2$/CO molar ratio of at least above 1.75 which latter gas has been obtained by subjecting a small portion of the feed for the first stage to a high temperature (above 325° C.) CO-shift.

7 Claims, No Drawings

PROCESS FOR THE PREPARATION OF ORGANIC COMPOUNDS

BACKGROUND OF THE INVENTION

The invention relates to a two-step process for the preparation of organic compounds from a mixture of hydrogen and carbon monoxide.

Organic compounds, such as aromatic hydrocarbons, paraffinic hydrocarbons and oxygen-containing compounds, particularly methanol, ethanol and dimethyl ether, can be prepared by catalytic conversion of $H_2/CO$ mixtures.

Aromatic hydrocarbons may be prepared, for instance, by contacting a $H_2/CO$ mixture having a $H_2/CO$ molar ratio lower than 2.0 with a bifunctional catalyst combination comprising one or more metal components having catalytic activity for the conversion of a $H_2/CO$ mixture into acyclic hydrocarbons and/or acyclic oxygen-containing organic compounds and a crystalline metal silicate capable of catalyzing the conversion of acyclic hydrocarbons and acyclic oxygen-containing organic compounds into aromatic hydrocarbons, with the understanding that if the $H_2/CO$ mixture has a $H_2/CO$ molar ratio lower than 1.5, a trifunctional catalyst combination is used which comprises one or more metal components having catalytic activity for the conversion of a $H_2/CO$ mixture into acyclic hydrocarbons and/or acyclic oxygen-containing organic compounds, one or more metal components having CO-shift activity and the crystalline metal silicate mentioned hereinbefore. An investigation into this process has shown that it has two drawbacks. In the first place, when using space velocities acceptable in actual practice, the conversion of the $H_2/CO$ mixtures leaves much to be desired. Further, the process yields a product consisting substantially of hydrocarbons having at most 12 carbon atoms in the molecule, and but a very small proportion of hydrocarbons having more than 12 carbon atoms in the molecule.

Continued research into this process has shown that the two drawbacks mentioned hereinabove can be overcome by contacting, in a second process step, hydrogen and carbon monoxide present in the reaction product of the process, together with other components of that reaction product, if desired, with a catalyst containing one or more metal components having activity for the conversion of a $H_2/CO$ mixture into paraffinic hydrocarbons, the metal components having been chosen from the group formed by cobalt, nickel and ruthenium, provided that the feed for the second step is made to have a $H_2/CO$ molar ratio of 1.75-2.25. What is achieved in this way is not only that, at space velocities acceptable in actual practice, a very high conversion of the $H_2/CO$ mixture is obtained, but also that a considerable proportion of the reaction product consists of hydrocarbons of having more than 12 carbon atoms in the molecule. The reason of the second step of the process is that the CO present in the feed for the second step as much as possible is converted into paraffinic hydrocarbons. To this end the $H_2/CO$ molar ratio of the feed for the second step should be 1.75-2.25. In some cases, for instance when a $H_2/CO$ mixture with a high $H_2/CO$ molar ratio is available for the process, the first step may yield a reaction product which has a $H_2/CO$ molar ratio of 1.75-2.25 and is suitable without further treatment for use as the feed for the second step. In most cases, however, the first step will yield a product having a $H_2/CO$ molar ratio lower than 1.75 and special measures will have to be taken to ensure that the feed which is contacted with the catalyst in the second step has the desired $H_2/CO$ molar ratio of 1.75-2.25.

An investigation has been made into six measures which might be suitable for the purpose. The measures examined were the following:

(1) Water may be added to the feed for the first step and the trifunctional catalyst combination mentioned hereinbefore may be used in the first step. Under the influence of the CO-shift activity of the trifunctional catalyst combination the added water reacts with CO from the feed to form a $H_2/CO_2$ mixture. This measure has the drawback that the activity of the catalyst combination is adversely affected both by the presence of the added water and by the presence of the carbon dioxide produced.

(2) The feed for the first step, together with water, may be subjected to CO-shift in a separate reactor. Since the CO-shift is an equilibrium reaction, the reaction product will contain unconverted water. Besides, the reaction product will contain carbon dioxide formed. As already stated in the discussion of the first measure, water and carbon dioxide have an adverse effect on the activity of the catalyst combination in the first step. Since, in view of the high cost involved, the removal of water and carbon dioxide from the CO-shift reaction product is not suitable for use on a technical scale, this second measure has the same drawback as that mentioned for the first measure.

(3) From the feed for the second step having a low $H_2/CO$ molar ratio so much CO may be separated that the desired $H_2/CO$ molar ratio is attained. In view of the high cost attending separation of CO from the feed for the second step, this measure is not suitable for use on a technical scale.

(4) To the feed for the second step having a low $H_2/CO$ molar ratio so much $H_2$ may be added that the desired $H_2/CO$ molar ratio is attained. Since the hydrogen required is not formed in the process, it will have to be supplied to the process from outside, which is a costly affair and, therefore, is not suitable for use on a technical scale.

(5) Water may be added to the feed for the second step and in the second step a bifunctional catalyst combination may be used which, in addition to metal components having catalytic activity for the conversion of a $H_2/CO$ mixture into paraffinic hydrocarbons, contains one or more metal components having CO-shift activity. The bifunctional catalyst combination used in the second step is usually composed of two separate catalysts, which, for convenience, will be referred to as catalysts A and B. Catalyst A is the Co-, Ni- or Ru-containing catalyst and catalyst B is the CO-shift catalyst. For the use of a bifunctional catalyst combination in the second step, the following four embodiments may be considered.

(5a) Carrying out the second step in a reactor containing a physical mixture of catalysts A and B.

(5b) Carrying out the second step in a reactor containing a fixed catalyst bed consisting of a layer of catalyst B, followed by a layer of catalyst A, both catalysts being used at the same temperature.

(5c) A procedure substantially corresponding with that described under (5b), but in which catalyst B, is used at a higher temperature than catalyst A.

(5d) Carrying out the second step in two separate reactors, the first containing catalyst B, the second catalyst A, and the temperature used in the first reactor being higher than that used in the second reactor.

Each of these embodiments has its drawbacks, which have to do with the type of CO-shift catalyst to be used. On the basis of the temperatures at which they are active, CO-shift catalysts can be divided into two groups, viz. "high-temperature CO-shift catalysts" (active at temperatures of about 325°–500° C.) and "low-temperatures CO-shift catalysts" (active at temperatures of about 175°–250° C.). Low-temperature CO-shift catalysts are particularly suitable for use with $H_2/CO$ mixtures already having a high $H_2/CO$ molar ratio, where a low conversion is sufficient to attain the purpose in view. Such $H_2/CO$ mixtures may very suitably be prepared from $H_2/CO$ mixtures having a low $H_2/CO$ molar ratio, by subjecting them to a high-temperature CO-shift. For attaining a high conversion in the case of $H_2/CO$ mixtures having a low $H_2/CO$ molar ratio (as described in the case of the feed for the second step of the process) the low temperature CO-shift catalysts are not very suitable, since, at the desired high conversion level, they are deactivated rapidly and also because at the low temperatures used, they tend to form methanol from low-hydrogen $H_2/CO$ mixtures. High-temperature CO-shift catalysts, when applied to low-hydrogen $H_2/CO$ mixtures, give a high conversion without being subject to rapid deactivation, and at the high temperatures used they show no tendency towards the formation of methanol. Since the temperature at which catalyst A is used in the second step of the process should be lower than 325° C., only a low-temperature CO-shift catalyst is eligible as catalyst B, when a bifunctional catalyst combination is to be used in the way described under (5a) and (5b). As stated hereinabove, this has serious disadvantages in view of rapid deactivation and undesirable methanol formation. The embodiments mentioned under (5c) and (5d) offer the possibility of using a high-temperature CO-shift catalyst as catalyst B, but this involves another drawback connected with the composition of the reaction product from the first step. This product usually contains a certain percentage of lower olefins. Separation of these lower olefins from the reaction product of the first step cannot be considered for use in a technical scale in view of the high cost involved. This means that the feed for the second step will, in addition to hydrogen and carbon monoxide, as a rule contain lower olefins. These lower olefins often cause rapid deactivation of the high-temperature CO-shift catalyst.

(6) So much of a hydrogen-rich $H_2/CO$ mixture may be added to the feed for the second step having a low $H_2/CO$ molar ratio, that the desired $H_2/CO$ molar ratio is reached. On the face of it, this measure, which is related to that mentioned under (4), seems unfit for use on a technical scale as well, as the required hydrogen-rich $H_2/CO$ mixture is not formed in the process and has to be supplied to the process from outside. A favorable circumstance, however, lies in the fact that in the two-step process a low-hydrogen $H_2/CO$ mixture is available as the feed for the first step. By separating a portion of this low-hydrogen $H_2/CO$ mixture and subjecting it to CO-shift, a reaction product having a high $H_2/CO$ molar ratio can be prepared in a simple way. In addition to hydrogen and carbon monoxide, this reaction product will contain unconverted water and carbon dioxide formed. Since the activity of the catalyst used in the second step of the process, in contrast to that of the catalyst combination in the first step, is hardly susceptible to the presence of water and carbon dioxide in the feed, this reaction mixture can be used as mixing component for the feed for the second step without water and dioxide having to be removed. In view of the drawbacks, described under 5, connected with the application of a low-temperature CO-shift to low-hydrogen $H_2/CO$ mixtures, only a high-temperature CO-shift is eligible for the present purpose. The present patent application relates to the application of a CO-shift, at a temperature above 325° C., to a low-hydrogen $H_2/CO$ mixture which has been separated from the feed for the first step of the two-step process described hereinabove and to the use of the hydrogen rich $H_2/CO$ mixture prepared as a mixing component for the feed for the second step of the process.

As was remarked hereinbefore, catalytic conversion of $H_2/CO$ mixtures can be used to prepare not only aromatic hydrocarbons, but also very suitable paraffinic hydrocarbons and oxygen-containing organic compounds.

Paraffinic hydrocarbons may be prepared, for instance, by contacting a $H_2/CO$ mixture having a molar ratio below 2.0 with an iron-containing bifunctional catalyst or catalyst combination which, in addition to activity for the conversion of a $H_2/CO$ mixture into, substantially, paraffinic hydrocarbons, has CO-shift activity. An investigation into this process has shown that the use of high space velocities presents difficulties. When the process is used for the conversion of $H_2/CO$ mixtures having a $H_2/CO$ molar ratio below 1.0, the stability of the bifunctional catalyst or catalyst combination leaves much to be desired. When the process is used for the conversion of $H_2/CO$ mixtures having a $H_2/CO$ molar ratio between 1.0 and 2.0, the conversion attained is low.

Oxygen-containing organic compounds may be prepared, for instance, by contacting a $H_2/CO$ mixture having a $H_2/CO$ molar ratio below 2.0, with a catalyst containing one or more metal components with catalytic activity for the conversion of a $H_2/CO$ mixture into oxygen-containing organic compounds. A drawback to these reactions is the fact that they are highly limited thermodynamically, so that a considerable proportion of the $H_2/CO$ mixture is not converted. According as higher space velocities are used, the conversion obtained are lower.

SUMMARY OF THE INVENTION

An investigation has shown that the above-mentioned drawbacks attending the preparation of paraffinic hydrocarbons and oxygen-containing organic compounds starting from $H_2/CO$ mixture having a $H_2/CO$ molar ratio below 2.0, as well as those attending the preparation or aromatic hydrocarbons from such a feed, can be overcome by contacting hydrogen and carbon monoxide present in the reaction product of the process, optionally together with other components from this reaction product, with a catalyst containing one or more metal components having catalytic activity for the conversion of a H₂/CO mixture into paraffinic hydrocarbons, which components originate from the group formed by cobalt, nickel and ruthenium, provided that care is taken that the feed for the second step has a H$_2$/CO molar ratio of 1.75-2.25. As with the preparation of aromatic hydrocarbons, the preparation of paraffinic hydrocarbons and oxygen-containing organic compounds from H$_2$/CO mixture having a H$_2$/CO molar ratio below 2.0, will often result in a product from the first step having a molar ratio lower than 1.75. In these cases, too, in order to raise the H$_2$/CO molar ratio of the feed for the second step, a hydrogen-rich H$_2$/CO mixture can very suitably be used as mixing component, the H$_2$/CO mixture having been prepared by subjecting a low-hydrogen H$_2$/CO mixture, separated from the feed for the first step of the two-step process, to a CO-shift at a temperature above 325° C.

The measure according to the invention may be used both in cases where the reaction product from the first step has a H$_2$/CO molar ratio below 1.75 and in cases where the reaction product from the first step already has a H$_2$/CO molar ratio of at least 1.75 (e.g. 1.8), but where it is desirable for the feed for the second step to have a higher H$_2$/CO molar ratio (e.g. 2.1).

The present patent application therefore relates to a process for the preparation, in two steps, of organic compounds from a mixture of carbon monoxide and hydrogen, in which a H$_2$/CO mixture having a H$_2$/CO molar ratio below 2.0 is divided into two portions, A and B, having the same composition, in which in the first step portion A, through contact with a catalyst comprising one or more metal components having catalytic activity for the conversion of a H$_2$/CO mixture into hydrocarbons and/or oxygen-containing organic compounds, is converted into a reaction mixture containing hydrogen and carbon monoxide, the H$_2$/CO molar ratio (R$_1$) of which is lower than 2.25, in which the H$_2$/CO molar ratio of portion B is raised to a value R$_2$ which is higher than R$_1$ and also higher than 1.75, by contacting portion B, together with water, at a temperature above 325° C., with a catalyst having CO-shift activity, in which hydrogen and carbon monoxide present in the reaction product prepared from portion A, together with other components from this reaction product, if desired, are mixed with the reaction product prepared from portion B to form a mixture having a H$_2$/CO molar ratio of 1.75-2.25, and in which the mixture thus obtained is contacted in the second step with a catalyst comprising one or more metal components with activity for the conversion of a H$_2$/CO mixture into paraffinic hydrocarbons, which metal components have been chosen from the group formed by cobalt, nickel and ruthenium.

DESCRIPTION OF PREFERRED EMBODIMENTS

In the process according to the invention organic compounds are prepared starting from a H$_2$/CO mixture having a H$_2$/CO molar ratio lower than 2.0. Such H$_2$/CO mixtures may very suitably be obtained by steam gasification of a carbonaceous material. Examples of such materials are brown coal, anthracite, coke, crude mineral oil and fractions thereof, as well as oils produced from tar sand and bituminous shale. The steam gasification is preferably carried out at a temperature of from 900°-1500° C. and a pressure of from 10-100 bar. In the process according to the invention the starting material is preferably a H$_2$/CO mixture having a H$_2$/CO molar ratio above 0.25.

If the process according to the invention is intended for the preparation of aromatic hydrocarbons, the catalyst used in the first step is a bi- of trifunctional catalyst which, in addition to the metal components having catalytic activity, comprises a crystalline metal silicate which is capable of catalyzing the conversion of acyclic hydrocarbons and acyclic oxygen-containing organic compounds into aromatic hydrocarbons. The said crystalline metal silicates are characterized in that, after one hour's calcination in air at 500° C., they have the following properties:

(a) thermally stable up to a temperature of at least 600° C., (b) an X-ray powder diffraction pattern in which the four lines in Table A are the strongest lines.

TABLE A

| d (Å) | Relative intensity |
|---|---|
| 11.1 ± 0.2 | VS |
| 10.0 ± 0.2 | VS |
| 3.84 ± 0.07 | S |
| 3.72 ± 0.06 | S | in which the letters used have the following meanings: VS=very strong; S=strong, and (c) which, in addition to oxides of hydrogen, alkali metal and/or alkaline-earth metal and silicon, comprises one or more oxides of a trivalent metal A chosen from the group formed by aluminum, iron, gallium, rhodium, chromium and scandium, the SiO$_2$/A$_2$O$_3$ molar ratio (for the sake of brevity hereinafter referred to as m) is higher than 10.

The expression "thermally stable up to a temperature of at least t° C.", used in this patent application, means that, upon heating of the silicate to a temperature of t° C., the X-ray powder diffraction pattern of the silicate remains substantially unchanged.

Although, basically, the crystalline silicates may contain more than one metal A, for the process according to the invention it is preferred to use catalysts in which the silicate contains only one metal A and in particular silicates containing aluminum, iron or gallium as the metal. The crystalline silicates used in the bi- and trifunctional catalyst combinations should have a value of m that is higher than 10. Preferably crystalline silicates are used in which m is lower than 1000. The crystalline silicate used in the bi- and trifunctional catalyst combinations is defined, among other things, with the aid of the X-ray powder diffraction pattern. In this pattern the strongest lines should be the four lines listed in Table A. The complete X-ray powder diffraction pattern of a typical example of a silicate applicable in the process according to the invention is given in Table B.

TABLE B

| d(Å) | Rel. int. | d(Å) | Rel. int. |
|---|---|---|---|
| 11.1 | 100 | 3.84 (D) | 57 |
| 10.0 (D) | 70 | 3.70 (D) | 31 |
| 8.93 | 1 | 3.63 | 16 |
| 7.99 | 1 | 3.47 | 1 |
| 7.42 | 2 | 3.43 | 5 |
| 6.68 | 7 | 3.34 | 2 |
| 6.35 | 11 | 3.30 | 5 |
| 5.97 | 17 | 3.25 | 1 |
| 5.70 | 7 | 3.05 | 8 |
| 5.56 | 10 | 2.98 | 11 |
| 5.35 | 2 | 2.96 | 3 |

TABLE B-continued

| d(Å) | Rel. int. | d(Å) | Rel. int. |
|---|---|---|---|
| 4.98 (D) | 6 | 2.86 | 2 |
| 4.60 | 4 | 2.73 | 2 |
| 4.35 | 5 | 2.60 | 2 |
| 4.25 | 7 | 2.48 | 3 |
| 4.07 | 2 | 2.40 | 2 |
| 4.00 | 4 | | |

(D) = doublet

The crystalline silicates may be prepared starting from an aqueous mixture comprising the following compounds: one or more compounds of an alkali metal or alkaline-earth metal (M), one or more compounds containing an organic cation (R) or from which such a cation is formed during the preparation of the silicate, one or more silicon compounds and one or more compounds comprising a trivalent metal A. The preparation is carried out by maintaining the mixture at an elevated temperature until the silicate has formed and subsequently separating the silicate crystals from the mother liquor and calcining them. In the aqueous mixture from which the silicates are prepared, the various compounds should be present in the following ratios, expressed in moles of the oxides:

$M_{2/n}O : R_2O = 0.1-20$,
$R_2O : SiO_2 = 0.01-0.5$,
$SiO_2 : A_2O_3 > 10$, and
$H_2O : SiO_2 = 5-50$; (n = the valency of M).

In the preparation of the silicates the base material preferred is a starting mixture in which M is present in an alkali metal compound and R in a tetra-alkylammonium compound, and in particular a starting mixture in which M is present in a sodium compound and R in a tetrapropylammonium compound. The crystalline silicates prepared in the way described hereinabove contain alkali metal and/or alkaline-earth metal ions. By suitable exchange methods these may be replaced by other cations, such as hydrogen ions or ammonium ions. The crystalline silicates used in the bi- and trifunctional catalyst combinations preferably have an alkali metal content below 0.1 %w and in particular below 0.05 %w. Although the trifunctional catalyst combinations are described in the present patent application as catalyst combinations comprising one or more metal components having catalytic activity for the conversion of a $H_2/CO$ mixture into acyclic hydrocarbons and/or acyclic oxygen-containing organic compounds, and one or more metal components having CO-shift activity, this certainly does not mean that the trifunctional catalyst combinations should invariably comprise individual metal components, each having one of the two catalytic functions. For, it has been found that metal components and combinations of metal components with catalytic activity for the conversion of a $H_2/CO$ mixture into substantially acyclic oxygen-containing organic compounds, often also have sufficient CO-shift activity, so that in such cases it is, usually, sufficient for one metal component or a combination of metal components to be incorporated into the trifunctional catalyst combinations. Metal components and combinations of metal components having catalytic activity for the conversion of a $H_2/CO$ mixture into substantially acyclic hydrocarbons, often have insufficient or no CO-shift activity at all. Therefore, when such metal components or combinations of metal components are used in the trifunctional catalyst combinations, in most cases one or more separate metal components having CO-shift activity should be incorporated.

The bi- and trifunctional catalyst combinations used in the first step of the process according to the invention for the preparation of aromatic hydrocarbons are preferably composed of two or three separate catalyst, which, for convenience, will be referred to as catalysts X, Y and Z. Catalyst X is the catalyst comprising the metal components having catalytic activity for the conversion of a $H_2/CO$ mixture into acyclic hydrocarbons and/or acyclic oxygen-containing compounds. Catalyst Y is the crystalline silicate. Catalyst Z is the catalyst comprising the metal components having CO-shift activity. As has been explained hereinbefore, in the trifunctional catalyst combinations the use of catalyst Z may in a number of cases be omitted.

Catalysts X which are capable of converting a $H_2/CO$ mixture into substantially acyclic hydrocarbons are known in the literature as Fischer-Tropsch catalysts. Such catalysts comprise one or more metals from the iron group or ruthenium together with one or more promoters for increasing the activity and/or the selectivity and, sometimes, a carrier material such as kieselguhr. If in the first step of the process according to the invention a bi- or trifunctional catalyst combination is used having a Fischer-Tropsch catalyst as the catalyst A, an iron catalyst or a cobalt catalyst is preferably chosen for the purpose, in particular such a catalyst prepared by impregnation. Very suitable catalysts for the purpose are:

(a) Catalysts comprising 30–75 pbw of iron and 5–40 pbw of magnesium per 100 pbw of alumina and prepared by impregnation of an alumina carrier with one or more aqueous solutions of salts of iron and of magnesium, followed by drying of the composition, calcination at a temperature of 700°–1200° C. and reduction. Special preference is given to catalysts of this type which, in addition to 40–60 pbw of iron and 7.5–30 pbw of magnesium, comprise 0.5–5 pbw of copper as a reduction promoter and 1–5 pbw of potassium as a selectivity promoter per 100 pbw of alumina and which have been calcined at 750°–800° C. and reduced at 250°–350° C.

(b) Catalysts comprising 10–40 pbw of iron and 0.25–10 pbw of chromium per 100 pbw of silica and prepared by impregnation of a silica carrier with one or more aqueous solutions of salts or iron and of chromium followed by drying of the composition, calcination and reduction at a temperature of from 350°–750° C. Special preference is given to catalysts of this type which, in addition to 20–35 pbw of iron and 0.5–5 pbw of chromium, comprise 1–5 pbw of potassium as a selectivity promoter and which have been calcined at 350°–750° C. and reduced at 350°–500° C.

(c) Catalysts comprising 10–40 pbw of cobalt and 0.25–5 pbw of zirconium, titanium or chromium per 100 pbw of silica and prepared by impregnation of a silica carrier with one or more aqueous solutions of salts of cobalt and zirconium, titanium or chromium, followed by drying of the composition, calcination at 350°–750° C. and reduction at 200°–350° C.

When the iron catalysts mentioned under (a) and (b) are used as catalysts X, the use of a catalyst Z in the trifunctional catalyst combinations may be omitted. When the cobalt catalysts mentioned under (c) are used as catalysts X, a catalyst Z should also be incorporated into the trifunctional catalyst combinations. If in the first step of the process according to the invention a bi- or trifunctional catalyst combination is used in which catalyst X is a Fischer-Tropsch catalyst, an iron catalyst as described under (a) and (b) is preferably used for the purpose. The first step of the process according to the invention for the preparation of aromatic hydrocarbons is preferably carried out at a temperature of from 200°–500° C. and in particular of from 250°–450° C., a pressure of from 1–150 bar and in particular of from 5–100 bar and a space velocity of from 50–5000 and in particular of from 300–3000 Nl gas/l catalyst/hour.

If the process according to the invention is to be used for the preparation of paraffinic hydrocarbons, then in the first step an iron-containing bi-functional catalyst or catalyst combination is used which, in addition to activity for the conversion of a $H_2/CO$ mixture into substantially paraffinic hydrocarbons, has CO-shift activity. Preferably, in the first step of the process use is made of a bi-functional catalyst comprising iron on a carrier, which has been prepared by impregnation. Examples of such catalysts are the Fe/Mg and Fe/Cr catalysts mentioned hereinabove under (a) and (b). The first step of the process according to the invention for the preparation of paraffinic hydrocarbons is preferably carried out at a temperature of from 200°–350° C. and in particular of from 250°–350° C., a pressure of from 10–70 bar and in particular of from 20–50 bar and a space velocity of from 500–5000 and in particular of from 500–2500 Nl gas/l catalyst/hour.

If the process according to the invention is to be used for the preparation of oxygen-containing organic compounds, then in the first step a catalyst is used which contains one or more metal components having catalytic activity for the conversion of a $H_2/CO$ mixture into oxygen-containing organic compounds. Preferably, in the first step a catalyst is used which is capable of converting a $H_2/CO$ mixture into substantially methanol and dimethylether. Examples of suitable catalysts capable of converting a $H_2/CO$ mixture into substantially methanol are catalysts comprising:

(1) zinc oxide and chromium oxide,
(2) copper, zinc oxide and chromium oxide,
(3) copper, zinc oxide and aluminum oxide, and
(4) copper, zinc oxide and oxides of rare earths.

Examples of suitable catalysts capable of converting a $H_2/CO$ mixture into substantially dimethyl ether are catalysts containing any one of the methanol synthesis functions mentioned under (1)–(4) and, in addition, an acid function, such as a physical mixture of $\alpha$-alumina and a composition comprising copper, zinc oxide and chromium oxide. Preferably, the first step of the process according to the invention for the preparation of oxygen-containing organic compounds is carried out at a temperature of from 175°–325° C., a pressure of from 30–300 bar and in particular of from 50–150 bar.

The oxygen-containing organic compounds which can be prepared in the first step of the two-step process according to the invention can very suitably be used as the starting material for the catalytic conversion into lower olefins and/or aromatic hydrocarbons. Catalysts very suitable for the purpose are the crystalline metal silicates described hereinbefore.

In the process according to the invention hydrogen and carbon monoxide present in the reaction product from the first step are used, together with other components of this reaction product, if desired, as feed for the second step. Optionally, the complete reaction product from the first step may be used as the feed for the second step. Before this feed is contacted with the catalyst in the second step, its $H_2/CO$ molar ratio ($R_1$), which is below 2.25, is raised to a value lying between 1.75 and 2.25 by mixing the feed with a $H_2/CO$ mixture having a $H_2/CO$ molar ratio ($R_2$) which is higher than 1.75, the latter $H_2/CO$ mixture having been obtained by separating a portion from the low-hydrogen $H_2/CO$ mixture available as feed for the first step of the process, mixing this portion with water and contacting the mixture, at a temperature above 325° C., with a catalyst having CO-shift activity. The percentage of low-hydrogen $H_2/CO$ mixture to be separated from the feed for the first step of the process and to be subjected to the high-temperature CO-shift, is dependent on the $H_2/CO$ molar ratio of that mixture, the percentage of $H_2/CO$ mixture present in the reaction product from the first step and its $H_2/CO$ molar ratio, the desired $H_2/CO$ molar ratio of the feed for the second step and the conversion attained in the high-temperature CO-shift. If all the other parameters are considered to be constant, the proportion of low-hydrogen $H_2/CO$ mixture to be separated from the feed for the first step of the process will be smaller according as the conversion attained in the high-temperature CO-shift is higher. In view of the desirability for the largest possible part of the available low-hydrogen $H_2/CO$ mixture to be used as feed for the first step of the process, and therefore for the smallest possible part to be subjected to CO-shift, it is advisable to aim at the highest possible conversion in the CO-shift reaction. By preference the CO-shift is carried out in such a way that it yields a product having a $H_2/CO$ molar ratio higher than 3 and in particular higher than 4. Suitable conditions for carrying out the CO-shift reaction are a temperature of from 325°–540° C. and in particular of from 10–75 bar and a space velocity of from 1000–50000 Nl. $l^{-1}.h^{-1}$ and in particular of from 200–10000 Nl. $l^{-1}.h^{-1}$. The high-temperature CO-shift catalyst used by preference is a chromium-containing catalyst. Particular preference is given to catalysts which, in addition to chromium, comprise either iron or zinc.

In the second step of the process according to the invention the feed which has been mixed with the hydrogen-rich $H_2/CO$ mixture to raise its $H_2/CO$ molar ratio to a value of from 1.75–2.25, is contacted with a catalyst comprising one or more metal components with activity for the conversion of a $H_2/CO$ mixture into paraffinic hydrocarbons, which metal components have been chosen from the group formed by cobalt, nickel and ruthenium. Preference is given to a cobalt catalyst and in particular a catalyst which comprises cobalt on a carrier and has been prepared by impregnation. Very suitable catalysts for the present purpose are the zirconium-, titanium- or chromium-promoted cobalt impregnation catalysts described hereinabove under (c). The second step of the process according to the invention is preferably carried out at a temperature of from 125°–325° C. and in particular of from 175°–275° C. and a pressure of from 1–150 bar and in particular of from 5–100 bar.

It has been found that the use in the second step of the process of the zirconium-, titanium- or chromium-promoted cobalt impregnation catalysts mentioned hereinbefore yields a mixture of heavy paraffinic hydrocarbons eminently suitable for conversion, by hydrocracking, into a middle distillate in high yields. The hydrocracking operation is characterized by very low gas production and hydrogen consumption.

The invention is now elucidated with the aid of the following example, which is intended to be a complete specific embodiment of the invention and is not intended to be regarded as a limitation thereof.

EXAMPLE

In the investigation the following catalysts were used:

Catalyst 1
ZnO—$Cr_2O_3$ catalyst in which the atomic percentage of zinc, calculated on the sum of zinc and chromium, was 70%.

Catalyst 2
Crystalline aluminum silicate catalyst prepared as follows. A mixture of NaOH, amorphous silica, $NaAlO_2$ and $(C_3H_7)_4NOH$ in water having the following molar composition $$25SiO_2.0.04Al_2O_3.3Na_2O.4.5[(C_3H_7)_4N]_2O.450H_2O$$

was heated in an autoclave under autogenous pressure for 24 hours at 150° C. After cooling of the reaction mixture, the silicate formed was filtered off, washed with water until the pH of the wash water was about 8, dried at 120° C. and calcined for one hour in air at 500° C. The silicate has the following properties:

(a) thermally stable up to a temperature of at least 800° C.,
(b) an X-ray powder diffraction pattern substantially corresponding with that given in Table B,
(c) a $SiO_2/Al_2O_3$ molar ratio (m) of 225, and
(d) a crystallite size of 1250 nm.

This silicate was converted into the H-form by boiling with a 1.0 molar $NH_4NO_3$ solution, washing with water, boiling again with a 1.0 molar $NH_4NO_3$ solution and washing, drying and calcination.

Catalyst 3
$Fe_2O_3$—$Cr_2O_3$ catalyst comprising 10 %w $Cr_2O_3$.

Catalyst 4
Co/Zr/$SiO_2$ catalyst comprising 25 pbw cobalt and 1.8 pbw zirconium per 100 pbw silica and prepared by impregnation of a silica carrier with an aqueous solution comprising a cobalt salt and a zirconium salt, followed by drying of the composition, calcination at 500° C. and reduction at 280° C.

Catalyst 5
Fe/Mg/Cu/K/$Al_2O_3$ catalyst comprising 50 pbw iron, 20 pbw magnesium, 2.5 pbw copper and 4 pbw potassium per 100 pbw alumina and prepared by impregnation of an alumina carrier with an aqueous solution comprising an iron salt, a magnesium salt, a copper salt and a potassium salt, followed by drying of the composition, calcination at 800° C. and reduction at 325° C.

Catalyst mixture I
Physical mixture of catalyst 1 and catalyst 2 in a 5:1 weight ratio.

Catalysts 4 and 5 and catalyst mixture I were tested in the preparation, in two steps, of hydrocarbons from a $H_2/CO$ mixture having a $H_2/CO$ molar ratio of 0.5. The test was carried out in two reactors of 50 ml each, containing a fixed catalyst bed. Three experiments were carried out. In Experiments 2 and 3, part of the available $H_2/CO$ mixture with a $H_2/CO$ molar ratio of 0.5 was converted in a separate 50 ml reactor containing a fixed catalyst bed consisting of catalyst 3, into a reaction product with a $H_2/CO$ molar ratio of 5.7, which reaction product was mixed with the total reaction product from the first step. The mixtures thus obtained were used as feed for the second step. In Experiment 1, carried out without using a separate CO-shift, the total reaction product from the first step was used as feed for the second step. Experiment 1 falls outside the scope of the invention. It has been included in the patent application for comparison.

The results of the three experiments are stated in Table C.

TABLE C

| Experiment No. | 1 | 2 | 3 |
|---|---|---|---|
| First step | | | |
| Catalyst No. | I | I | 5 |
| Quantity of catalyst, ml | 12 | 10 | 6 |
| Feed, Nl. hour$^{-1}$ | 15.5 | 10 | 10 |
| $H_2/CO$ molar ratio of feed | 0.5 | 0.5 | 0.5 |
| Temperature, °C. | 375 | 375 | 280 |
| Pressure, bar | 60 | 60 | 30 |
| Conversion of $H_2/CO$ mixture, % v | 58 | 70 | 75 |
| $H_2/CO$ molar ratio of product | 0.5 | 0.5 | 0.32 |
| CO-shift reaction | | | |
| Catalyst No. | — | 3 | 3 |
| Quantity of catalyst, ml | — | 2 | 2 |
| Feed, Nl. hour$^{-1}$ | — | 5.5 | 5.7 |
| $H_2/CO$ molar ratio of feed | — | 0.5 | 0.5 |
| Quantity of water added, ml.h$^{-1}$ | — | 3.0 | 3.1 |
| Temperature, °C. | — | 350 | 350 |
| Pressure, bar | — | 60 | 60 |
| $H_2/CO$ molar ratio of product | — | 5.7 | 5.7 |
| Second step | | | |
| Catalyst No. | 4 | 4 | 4 |
| Quantity of catalyst, ml | 10 | 10 | 10 |
| $H_2/CO$ molar ratio of feed | 0.5 | 2 | 2 |
| Temperature, °C. | 230 | 230 | 230 |
| Pressure, bar | 60 | 60 | 60 |
| Total conversion of the $H_2/CO$ mixture (1st + 2nd step), % v | 78 | 94 | 95 |

We claim:

1. A two-step process for the preparation of organic compounds from a mixture of hydrogen and carbon monoxide, wherein a $H_2/CO$ mixture having a $H_2/CO$ molar ratio below 2.0 is divided into two portions, a larger portion A and a smaller portion B, of the same composition; in the first step portion A, through contact with a catalyst comprising one or more metal components having catalytic activity for the conversion of a $H_2/CO$ mixture into hydrocarbons and/or oxygen-containing organic compounds, is converted into a reaction mixture in which the $H_2/CO$ molar ratio ($R_1$) is lower than 2.25; and portion B, through contact, together with water, at a temperature above 325° C., with a catalyst having CO-shift activity, is converted into a reaction mixture in which the $H_2/CO$ molar ratio is higher than $R_1$ and also higher than 1.75; hydrogen and carbon monoxide present in the reaction product from portion A, optionally together with other components from this reaction product, are mixed with the reaction product from portion B to form a mixture having a $H_2/CO$ molar ratio of from 1.75–2.25; and in the second step the mixture thus obtained is contacted with a catalyst comprising one or more metal components having activity for the conversion of a $H_2/CO$ mixture into paraffinic hydrocarbons, which metal components have been chosen from the group formed by cobalt, nickel and ruthenium.

2. A process according to claim 1, wherein for the preparation of aromatic hydrocarbons the first step is carried out using a bifunctional catalyst combination comprising one or more metal components having catalytic activity for the conversion of a $H_2/CO$ mixture into acyclic hydrocarbons and/or acylic oxygen-containing organic compounds and a crystalline metal silicate which, after one hour's calcination in air at 500° C. has the following properties:

(a) thermally stable up to a temperature of at least 600° C.,
(b) an X-ray powder diffraction pattern in which the four lines listed in Table A are the strongest lines:

TABLE A

| d (Å) | Relative intensity |
|---|---|
| 11.1 ± 0.2 | VS |
| 10.0 ± 0.2 | VS |
| 3.84 ± 0.07 | S |
| 3.72 ± 0.06 | S | in which the letters used have the following meanings: VS=very stron; S=strong, and (c) in which, in addition to hydrogen, alkali metal and/or alkaline-earth metal and silicon, comprises one or more oxides of a trivalent metal A chosen from the group formed by aluminum, iron, gallium, rhodium, chromium and scandium, the $SiO_2/A_2O_3$ molar ratio (m) is higher than 10, with the understanding that if the $H_2/CO$ mixture has a $H_2/CO$ molar ratio lower than 1.5, the first step is carried out using a trifunctional catalyst combination comprising one or more metal components having catalytic activity for the conversion of a $H_2/CO$ mixture into acyclic hydrocarbons and/or acyclic oxygen-containing organic compounds, one or more metal components with CO-shift activity and the crystalline metal silicate mentioned hereinbefore.

3. A process according to claim 2, wherein the crystalline metal silicate comprises only one metal A chosen from the group formed by aluminum, iron and gallium and m has a value lower than 1000.

4. A process according to claim 2, wherein the first step is carried out using a catalyst combination comprising a mixture of the crystalline metal silicate and a catalyst chosen from the group formed by
  (a) catalysts which are capable of converting a $H_2/CO$ mixture into substantially methanol and/or dimethyl ether,
  (b) catalysts comprising 30–75 pbw iron and 5–40 pbw magnesium per 100 pbw alumina carrier with one or more aqueous solutions of salts of iron and of magnesium, followed by drying of the composition, calcination at a temperature of from 700°–1200° C., and reduction, and
  (c) catalysts comprising 10–40 pbw iron and 0.25–10 pbw chromium per 100 pbw silica and prepared by impregnation of a silica carrier with one or more aqueous solutions of salts of iron and of chromium, followed by drying of the composition, calcination and reduction at a temperature of from 350°–750° C.

5. A process according to claim 1, wherein for the preparation of paraffinic hydrocarbons, the first step is carried out using an iron-containing bifunctional catalyst or catalyst combination which, in addition to activity for the conversion of a $H_2/CO$ mixture into substantially paraffinic hydrocarbons, has CO-shift activity.

6. A process according to claim 1, wherein for the preparation of oxygen-containing organic compounds, the first step is carried out using a catalyst comprising one or more metal components having catalytic activity for the conversion of a $H_2/CO$ mixture into oxygen-containing organic compounds.

7. A process according to claim 6, wherein the first step is carried out using a catalyst which has the property of converting a $H_2/CO$ mixture into substantially methanol and/or dimethyl ether.

* * * * *